United States Patent [19]

Kurosaki et al.

[11] 4,350,645

[45] Sep. 21, 1982

[54] METHOD FOR PRODUCING A PHOSPHORIC MONOESTER

[75] Inventors: Tomihiro Kurosaki, Osaka; Akio Manba, Wakayama, both of Japan

[73] Assignee: Kao Soap Co., Ltd., Tokyo, Japan

[21] Appl. No.: 210,352

[22] Filed: Nov. 25, 1980

[30] Foreign Application Priority Data

Dec. 17, 1979 [JP] Japan .................................. 54-163791

[51] Int. Cl.$^3$ .............................................. C07F 9/141
[52] U.S. Cl. ..................................... 260/978; 260/980
[58] Field of Search ................................ 260/978, 980

[56] References Cited

U.S. PATENT DOCUMENTS 3,331,896  7/1967  Eiseman et al. ...................... 260/978

Primary Examiner—Anton H. Sutto
Attorney, Agent, or Firm—Oblon, Fisher, Spivak, McClelland & Maier

[57] ABSTRACT

A phosphoric monoester of an organic hydroxy compound can be produced in a high concentration in accordance with a two-step reaction. In a first step, the organic hydroxy compound is esterified in the presence of an excess amount of one or more phosphorylating agents selected from the group consisting of phosphorus pentoxide, phosphoric acid and polyphosphoric acids. A further portion of the same organic hydroxy compound is added, in a second step, to the reaction mixture of the first step to make the overall quantity of the organic hydroxy compound equivalent to its stoichiometric quantity.

8 Claims, No Drawings

METHOD FOR PRODUCING A PHOSPHORIC MONOESTER

BACKGROUND OF THE INVENTION

The present invention relates to a method for producing a phosphoric monoester by phosphorylating an organic hydroxy compound (hereinafter referred to as ROH). Particularly, the present invention is concerned with a method for producing phosphoric esters containing a monoester in a high concentration, which comprises a first step of esterification of ROH which esterification is conducted in the presence of an excess amount of a phosphoric acid component, and a second step of reaction which is conducted by adding a further portion of ROH to the reaction mixture of the first step to make the overall ROH equivalent to its stoichiometric quantity.

Acidic phosphoric esters of ROH and their alkali metal salts, ammonium salts, alkanolamine salts are widely used as cleansing agents, emulsifying agents, antistatic agents, rust inhibitors, etc.

Acidic phosphoric esters presently industrially widely used are each the equimolar mixture of a monoester(I) and a diester(II) (hereinafter referred to as a sesquiphosphate) prepared from ROH and phosphorus pentoxide.

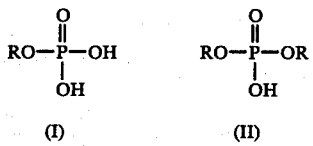

(I)            (II)

However, the monoester and the diester are quite different in their physical properties. For example, with respect to alkali metal salts and alkanolamine salts of a long chain alkylphosphate, the monoester thereof has good water solubility, good foaming property, good cleansing power and low toxicity and gives little irritation to the skin, and accordingly it provides an excellent cleansing agent, whereas the diester thereof is hardly soluble in water, exhibits little foaming power or rather has a defoaming property, and accordingly it can not be used as a high foaming cleansing agent. Accordingly, the sesquiphosphate does not provide the above properties of the monoester, and therefore can not be a substitute for the monoester where the properties of the monoester are required.

Thus, it is strongly desired to produce safely, easily and industrially a phosphoric ester having a high monoester content. There are some reports in this respect, as follows:

(1) A method which comprises hydrolysing a monoalkyl phosphorodichloride

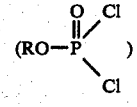

prepared by reacting ROH with phosphorus chloride. (Fuben Beil: Methoden der organischen Chemie, Vol. 12/2, p. 163-164, Japanese laid-open patent application No. 64226/75)

(2) A method which comprises adding water to ROH preliminarily and reacting phosphorus pentoxide therewith. (Japanese Patent Publication No. 14416/66)

(3) A method which comprises reacting an alcohol with orthophosphoric acid and phosphorus pentoxide separately or simultaneously. (Japanese Patent Publication No. 6730/67)

(4) A method which comprises reacting ROH with polyphosphoric acid [A. K. Nalson et al.: Inorganic Chemistry, Vol 2, 775–777 (1963), F. B. Clarke et al.: J. Am, Chem, Soc. 88, 4401–4405 (1966)]

However, the above mentioned methods have the following drawbacks and accordingly they are industrially disadvantageous.

The method identified by (1) produces 3 moles of hydrochloric acid to obtain 1 mole of the monoester, as shown by the following formulas, and accordingly there are difficult problems such as corrosion of the apparatus and disposal of the hydrochloric acid.

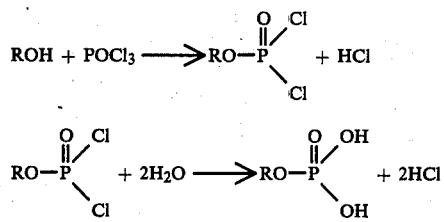

Further, the method (1) generates an alkyl chloride as a by-product, which adversely affects the yield of the monoester.

With respect to the methods (2) and (3) and referring to the proportion of the monoester and the diester, it is possible to increase the proportion of the monoester by increasing the amounts of water or orthophosphoric acid. However, then the yield of inorganic orthophosphoric acid will be extremely increased. Namely, the reaction rate of phosphoric acid is extremely low, and the product contains a great amount of inorganic orthophosphoric acid, which is undesirable in certain cases and thus limits the field of usage of the product.

In the method (4), the yield of inorganic orthophosphoric acid produced as a by-product of the reaction, almost corresponds to the reciprocal number of the average condensation degree of the polyphosphoric acid, and accordingly to order to minimize the yield of the inorganic orthophosphoric acid, it is necessary to use polyphosphoric acid having a very high condensation degree. However, it is extremely difficult to industrially produce such a high condensation polyphosphoric acid in view of the limitation in the materials for the vessel for its production.

SUMMARY OF THE INVENTION

Under these circumstances, the present inventors have conducted an extensive research on the methods for industrially producing a phosphoric monoester and as a result have accomplished the present invention.

Namely, the present invention provides a method for producing a phosphoric monoester which comprises reacting a mixture comprising (1) 1 mole, as calculated as $P_2O_5$, of one or more phosphorylating agents(A) selected from the group consisting of phosphorus pentoxide, phosphoric acid and a polyphosphoric acid, (2) 0.8 to 1.2 mole of water(B) including $nH_2O$ when said phosphorylating agents were represented by $P_2O_5 \cdot nH_2O$, and (3) 0.4 to (2.8−B) mole of an organic hydroxy compound(C), and then adding an organic hydroxy compound(D) to the reaction mixture for further reaction.

DETAILED DESCRIPTION OF THE PREFERRED EMBODIMENTS OF THE INVENTION

Although a broad aspect of this invention has been described in the immediately preceding paragraph, there may be mentioned, as the organic hydroxy compound (ROH) of the present invention, a saturated or unsaturated aliphatic alcohol of a $C_6$-$C_{30}$ straight or branched chain, or a $C_2$-$C_4$ alkylene oxide addition product (1 to 100 moles of the addition) of said aliphatic alcohol or an alkylphenol (the alkyl group having $C_6$-$C_{20}$).

The reaction of the first step of the present invention must be carried out with use of the phosphorylating agent, water and ROH in a proportion within the specified ranges. Successful results will not be obtained if the amounts are not within the specified ranges. Namely, the three components are used to satisfy the following formula, $$\frac{[\text{moles of ROH}(C)] + [\text{moles of water}(B)]}{[\text{moles of the phosphorylating agents}(A)] \text{ as calculated as } P_2O_5} = 1.2 \text{ to } 2.8$$

Where (A) is 1 mole, if water(B) is less than 0.8 mole, the yield of the diester increases, and if water (B) exceeds 1.2 mole, the yield of phosphoric acid rapidly increases thereby reducing the yield of the monoester and thus leading to an undesirable result. Further, ROH (C) is preferred to be within the above mentioned range, particularly, 0.5 to 1.5 mole per 1 mole of (A) [provided that the total of (C) and (B) is not more than 2.8 moles]. With increase of the proportion of ROH (C), the yield of the diester increases. Accordingly, in order to increase the proportion of the monoester relative to the diester, ROH should be used in a smaller amount. However, as the amount of ROH decreases, the viscosity rapidly increases to form a paste thus leading to operational difficulty.

The mixture thus prepared to have the specified proportion, is stirred for reaction at a temperature of 40° to 120° C., preferably 60° to 90° C. for 0.5 to 24 hours. When phosphoric acid or a polyphosphoric acid is used as the phosphating agent, it is industrially extremely difficult to use it alone for the preparation of the mixture having the above proportion, and accordingly, it is used in combination with phosphorus pentoxide. In this case, firstly predetermined amounts of ROH (C), water (B) including $nH_2O$ when phosphoric acid and polyphosphoric acid are represented by $P_2O_5.nH_2O$, and phosphoric acid or polyphosphoric acid will be mixed at a temperature of 30° to 100° C., preferably 40° to 80° C. for 0.5 to 5 hours, and then phosphorus pentoxide corresponding to the deficiency of the phosphorus component, will be added, and the reaction is carried out at 40° to 120° C., preferably 60° to 90° C. for 0.5 to 24 hours.

Next, ROH (D) is added to the product thus obtained, and the mixture is reacted at 40° to 120° C., preferably 60° to 90° C., for 0.5 to 24 hours, whereby phosphoric monoester is produced. The amount of ROH (D) to be added in this case, should preferably fall within the formula of $(B+C+D)/A$ being 2.9 to 3.1.

According to the above mentioned method of the present invention, phosphoric monoester can be prepared in an extremely high yield, which is considered to be based on the following reaction mechanism.

Namely, the reaction which forms a phosphoric monoester from ROH, $H_2O$ and $P_2O_5$, is represented by the following formula:

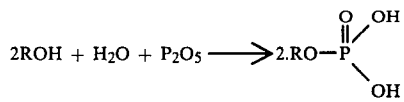

Accordingly, the relative stoichiometric amounts are as follows: $ROH:H_2O:P_2O_5 = 2:1:1$.

However, as mentioned above, it is not possible to obtain the phosphoric monoester in high yield by a method wherein such stoichiometric amounts of the reactants are reacted simultaneously (Comparative Example 1) or, even when the reaction is carried out in two steps as in the present invention, by a method wherein ROH and $P_2O_5$ are reacted in the first step in the absence of water, followed by the addition of water to complete the reaction of the second step (Comparative Example 2). Whereas, according to the present invention, the reaction of the first step is carried out in the presence of an excess amount of $P_2O_5$ within a predetermined range, whereby a substance represented by the formula

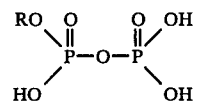

forms, and this substance reacts with ROH in the second step to produce the phosphoric monoester in high yield, as represented by the following formula.

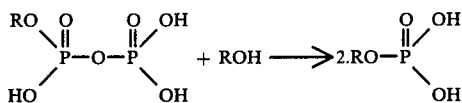

Now, the invention will further be described with reference to working Examples and Comparative Examples.

EXAMPLE 1

To 189.0 g of lauryl alcohol (1.0 mole, $OHv = 296.9 \rightarrow MW = 189.0$), 46.9 g of 85% phosphoric acid (1.0 mole of water, 0.203 mole of $P_2O_5$) were added and stirred at 40° C. for 1 hour. Then, 113.1 g of phosphorus pentoxide (0.797 mole of $P_2O_5$) were gradually added, and the reaction was carried out at 80° C. for 6 hours. To this reaction solution, 189.0 g of lauryl alcohol (1.0 mole) were added and the reaction was further carried out at 80° C. for 12 hours.

The reaction product thus obtained comprised 80.8 molar % of monolauryl phosphate, 7.7 molar % of dilauryl phosphate and 11.5 molar % of orthophosphoric acid.

The analysis of the reaction product was carried out in the following manner.

The phosphorus compounds obtained by the reaction are monolauryl phosphate, dilauryl phosphate and orthophosphoric acid. It is not possible to quantitatively analyse each component of the mixture by the potentiometric titration with alkali, since the third dissolution constant of the phosphoric acid is very small and the results tend to show the equivalence points of the first and second steps only. Accordingly, the measurement was done by a novel method for measurement developed by the present inventors [Reference is made to Japanese Patent Application No. 163792/1979 filed Dec. 17, 1979 by the same assignee as in this application and entitled "Method for analysis of organic phosphoric esters"].

Namely, 1 g of the reaction product was subjected to alkali titration of potential difference in a usual manner, to determine the amount of alkali (a mg) required to reach the first equivalence point and the amount of alkali (b mg) required to reach the second equivalence point, and further, after the addition of silver nitrate in an amount in excess of the stoichiometric amount of acidic —OH groups of phosphoric acid present in the reaction product, an alkali titration is carried out to determine the amount of alkali (c mg) required to reach the third equivalence point. The contents of the respective components are calculated in accordance with the following formulas:

$$\text{Monolauryl phosphate (molar \%)} = \frac{2b - a - c}{a} \times 100$$

$$\text{Dilauryl phosphate (molar \%)} = \frac{2a - b}{a} \times 100$$

$$\text{Orthophosphoric acid (molar \%)} = \frac{c - b}{a} \times 100$$

EXAMPLE 2

To 189.0 g of lauryl alcohol (1.0 mole), 18.0 g of water (1.0 mole) were added, and while stirring the mixture vigorously, 141.9 g of phosphorus pentoxide (1.0 mole of $P_2O_5$) were gradually added and the reaction was carried out at 80° C. for 3 hours. Then, 189.0 g of lauryl alcohol (1.0 mole) were added to the reaction solution, and the reaction was further carried out at 80° C. for 10 hours. The reaction product was analysed in the same manner as in Example 1 and found to comprise 80.5 molar % of monolauryl phosphate, 7.8 molar % of dilauryl phosphate and 11.7 molar % of orthophosphoric acid.

EXAMPLE 3

To 189.0 g of lauryl alcohol (1.0 mole), 107.7 g of 115% orthoequivalent (83.3% of $P_2O_5$) polyphosphoric acid (1.0 mole of water, 0.632 mole of $P_2O_5$) were added and reacted at 50° C. for 1 hour. To this reaction solution, 52.2 g of phosphorus pentoxide (0.368 mole of $P_2O_5$) were gradually added, and the reaction was carried out at 80° C. for 8 hours. To this reaction solution, 189.0 g of lauryl alcohol (1.0 mole) were added and the reaction was further carried out at 80° C. for 12 hours. The reaction product was analysed in the same manner as in Example 1 and found to comprise 82.1 molar % of monolauryl phosphate, 8.1 molar % of dilauryl phosphate and 9.9 molar % of orthophosphoric acid.

EXAMPLE 4

To 123.8 g of cetyl alcohol (0.5 mole, OHv=226.6→MW=247.6), 46.9 g of 85% phosphoric acid (1.0 mole of water, 0.203 mole of $P_2O_5$) were added and stirred at 60° C. for one hour. Then, 113.1 g of phosphorus pentoxide (0.797 mole of $P_2O_5$) was gradually added and the reaction was carried out at 80° C. for 6 hours. To this reaction solution, 371.4 g of cetyl alcohol (1.5 mole) were added and the reaction was further carried out for 12 hours. The reaction product thus obtained was analysed in the same manner as in Example 1 and found to comprise 84.0 molar % of monocetyl phosphate, 6.2 molar % of dicethyl phosphate and 9.7 molar % of orthophosphoric acid.

EXAMPLE 5

To $a_1$ g of lauryl alcohol (OHv=295.6→MW=189.8), b g of 85% phosphoric acid was added and homogeneously mixed at 40° C. To this mixture, c g of phosphorus pentoxide was gradually added while vigorously agitating at a temperature of not more than 70° C. The mixture was reacted at 80° C. for 6 hours to complete the reaction of the first step. To this reaction solution, $a_2$ g of lauryl alcohol was added, and the reaction was further carried out at 80° C. for 6 hours to complete the reaction of the second step.

The amounts of lauryl alcohol ($a_1$, $a_2$), and the phosphating agents (b, c) are presented in Table 1, and the proportions of the lauryl alcohol, water and $P_2O_5$ are presented in Table 2.

TABLE 1

| Experiments | $a_1$(g) | b(g) | c(g) | $a_2$(g) |
|---|---|---|---|---|
| 1 | 118.6 | 14.1 | 62.3 | 109.2 |
| 2 | 131.9 | 26.1 | 62.9 | 79.2 |
| 3 | 166.1 | 45.9 | 71.1 | 46.5 |

TABLE 2

| | Molar ratios | | |
|---|---|---|---|
| Experiments | Reaction of first step $ROH/H_2O/P_2O_5$ | Reaction of second step $ROH/H_2O/P_2O_5$ | Notes |
| 1 | 1.25/0.6/1.0 | 2.4/0.6/1.0 | Other than the present invention |
| 2 | 1.25/1.0/1.0 | 2.0/1.0/1.0 | Present invention |
| 3 | 1.25/1.4/1.0 | 1.6/1.4/1.0 | Other than the present invention |

The products obtained by Experiments 1 to 3, were analysed in the same manner as in Example 1 and the results are shown in Table 3.

TABLE 3

| | Experiments | | |
|---|---|---|---|
| Molar % | 1 | 2 | 3 |
| Monolauryl phosphate | 67.4 | 82.1 | 63.7 |
| Dilauryl phosphate | 26.9 | 8.1 | 8.3 |
| Orthophosphoric acid | 5.7 | 9.9 | 28.1 |

COMPARATIVE EXAMPLE 1

To 378.0 g of lauryl alcohol (2.0 moles, OHv=296.9→MW 189.0), 46.9 g of 85% phosphoric acid (1.0 mole of water, 0.203 mole of $P_2O_5$) were added and stirred at 40° C. for one hour. Then, 113.1 g of phosphorus pentoxide (0.797 mole of $P_2O_5$) were gradually added and the reaction was carried out at 80° C. for 18 hours. The reaction product was analysed in the same manner as in Example 1 and found to comprise 66.2 molar % of monolauryl phosphate, 18.9 molar % of dilauryl phosphate and 14.9 molar % of orthophosphoric acid.

COMPARATIVE EXAMPLE 2

To 378.0 g of lauryl alcohol (2.0 moles, OHv=296.9→MW=189.0), 141.9 g of phosphorus pentoxide (1.0 mole of $P_2O_5$) were gradually added and the reaction was carried out at 80° C. for 6 hours. To this reaction solution, 18.0 g of water (1.0 mole) was added and the reaction was further carried out at 80° C. for 12 hours.

The reaction product was analysed in the same manner as in Example 1 and found to comprise 57.4 molar % of monolauryl phosphate, 22.2 molar % of dilauryl phosphate, and 20.4 molar % of orthophosphoric acid.

What is claimed is:

1. A method for producing a phosphoric monoester comprising reacting a mixture of (1) a mole amount, calculated as $P_2O_5$, of one or more phosphorylating agents (A) selected from the group consisting of phosphorus pentoxide, phosphoric acid and polyphosphoric acid, (2) 0.8 to 1.2 per mole of phosphorylating agent of water (B) including $nH_2O$ when said phosphorylating agents are represented by $P_2O_5 \cdot nH_2O$, and (3) 0.4 to (2.8−B) mole of an organic hydroxy compound (C) per mole calculated as $P_2O_5$ of phosphorylating agent, and then adding an additional amount (D) of said organic hydroxy compound to the reaction mixture, the amount of D being derived from the equation:

$(B+C+D)/A = 2.9$ to $3.1$.

2. The method of claim 1 wherein said organic hydroxy compound is a saturated or unsaturated aliphatic alcohol of a $C_6$–$C_{30}$ straight or branched chain, or a $C_2$–$C_4$ alkylene oxide addition product (1 or 100 moles of the addition) of said aliphatic alcohol or an alkylphenol whose alkyl group has 6 to 20 carbon atoms.

3. The method of claim 1 or 2, wherein said phophorylating agent is selected from the group consisting of phosphorus pentoxide, phosphoric acid and mixtures thereof.

4. The method of claim 1, wherein said organic hydroxy compound is a saturated or unsaturated aliphatic alcohol having $C_{10}$–$C_{18}$ alkyl group.

5. The method of claim 1, wherein said mixture is reacted at 40° to 120° C. and for 0.5 to 24 hours.

6. The method of claim 5, wherein the mixture is reacted at 60° to 90° C.

7. The method of claim 1, wherein said method employs two phosphorylating agents selected from the group consisting of phosphorus pentoxide, phosphoric acid and polyphosphoric acid; and said organic hydroxy compound (C), water (B) and said phosphoric acid or polyphosphoric acid are first reacted at 30° to 100° C. for 0.5 to 5 hours, and then phosphorus pentoxide is combined with the resulting reaction mixture and reacted therewith at 40°–120° C. for 0.5 to 24 hrs.

8. The method of claim 7, wherein said organic hydroxy compound is further reacted at 40°–120° C. for 0.5–24 hours.